US00PP19156P2

(12) United States Plant Patent
Fischer-Tohl

(10) Patent No.: US PP19,156 P2
(45) Date of Patent: Aug. 26, 2008

(54) ***GERANIUM* PLANT NAMED 'SIL LINUS'**

(50) Latin Name: *Pelargonium zonale*
Varietal Denomination: Sil Linus

(75) Inventor: Ilse Fischer-Tohl, Kirchlintein (DE)

(73) Assignee: Silze GmbH & Company KG, Weener (DE)

( * ) Notice: Subject to any disclaimer, the term of this patent is extended or adjusted under 35 U.S.C. 154(b) by 0 days.

(21) Appl. No.: 11/974,694

(22) Filed: Oct. 16, 2007

Related U.S. Application Data

(60) Provisional application No. 60/900,011, filed on Feb. 7, 2007.

(51) Int. Cl.
*A01H 5/00* (2006.01)

(52) U.S. Cl. ..... Plt./328

(58) Field of Classification Search ..... Plt./328
See application file for complete search history.

(56) References Cited

PUBLICATIONS

UPOV–ROM search for PBR PEL 02046 for cultivar Sil Linus, p. 1.*

* cited by examiner

*Primary Examiner*—Annette H Para
(74) *Attorney, Agent, or Firm*—Audrey Charles

(57) ABSTRACT

A new and distinct cultivar of *Geranium* plant named 'Sil Linus', characterized by in semi-double type, very light pink-colored flowers with medium purple red-colored spots, dark green-colored foliage, and low to moderately vigorous, upright, compact, and bushy growth habit.

1 Drawing Sheet

Latin name of genus and species of plant claimed: *Pelargonium zonale.*
Variety denomination: 'Sil Linus'.

BACKGROUND OF THE INVENTION

The present invention relates to a new and distinct cultivar of *Geranium* plant botanically known as *Pelargonium zonale* and hereinafter referred to by the cultivar name 'Sil Linus'.

The new cultivar originated in a controlled breeding program in Weener, Germany during Summer 2001. The objective of the breeding program was the development of *Geranium* cultivars that have unique flower coloration, dark green-colored foliage, and a vigorous, upright-mounded growth habit.

The new *Geranium* cultivar is the result of cross-pollination. The female (seed) parent of the new cultivar is 'Kitty', not patented, characterized by its semi-double type light violet-colored flowers with small medium red-colored spots, dark green-colored foliage, and low to very low vigor, compact, and upright growth habit. The male (pollen) parent of the new cultivar is 'Lady', not patented, characterized by its semi-double type light pink-colored flowers with bright medium red-colored spots, dark green-colored foliage, and very low vigor, compact, and upright growth habit. The new cultivar was discovered and selected as a single flowering plant within the progeny of the above stated cross-pollination during June 2002 in a controlled environment at Weener, Germany.

Asexual reproduction of the new cultivar by terminal stem cuttings since June 2002 at Weener, Germany and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'sil Linus' as a new and distinct cultivar of *Geranium* plant:

1. Semi-double type, very light pink-colored flowers with medium purple red-colored spots;
2. Dark green-colored foliage; and
3. Low to moderately vigorous, upright, compact, and bushy growth habit.

Plants of the new cultivar differ from plants of the female parent primarily in flower color and growth vigor and from plants of the male parent primarily in flower color and growth vigor.

Of the many commercially available *Geranium* cultivars, the most similar in comparison to the new cultivar is Americana Light Pink Splash II 'Amri Light Pink Spla II' U.S. Plant Pat. No. 12,944. However, in side by side comparisons, plants of the new cultivar differ from plants of 'Amri Light Pink Spla II' in the following characteristics:

1. Plants of the new cultivar have a leaf color different from plants of 'Amri Light Pink Spla II';
2. Plants of the new cultivar have a flower color different from plants of 'Amri Light Pink Spla II';
3. Plants of the new cultivar are taller than plants of 'Amri Light Pink Spla II'; and
4. Plants of the new cultivar have fewer umbels than plants of 'Amri Light Pink Spla II'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sil Linus'. The plants were grown in 4.5 inch pots for 10 weeks in a greenhouse at West Chicago, Ill. Plants were given one pinch at transplant.

DETAILED BOTANICAL DESCRIPTION

Figure 1:
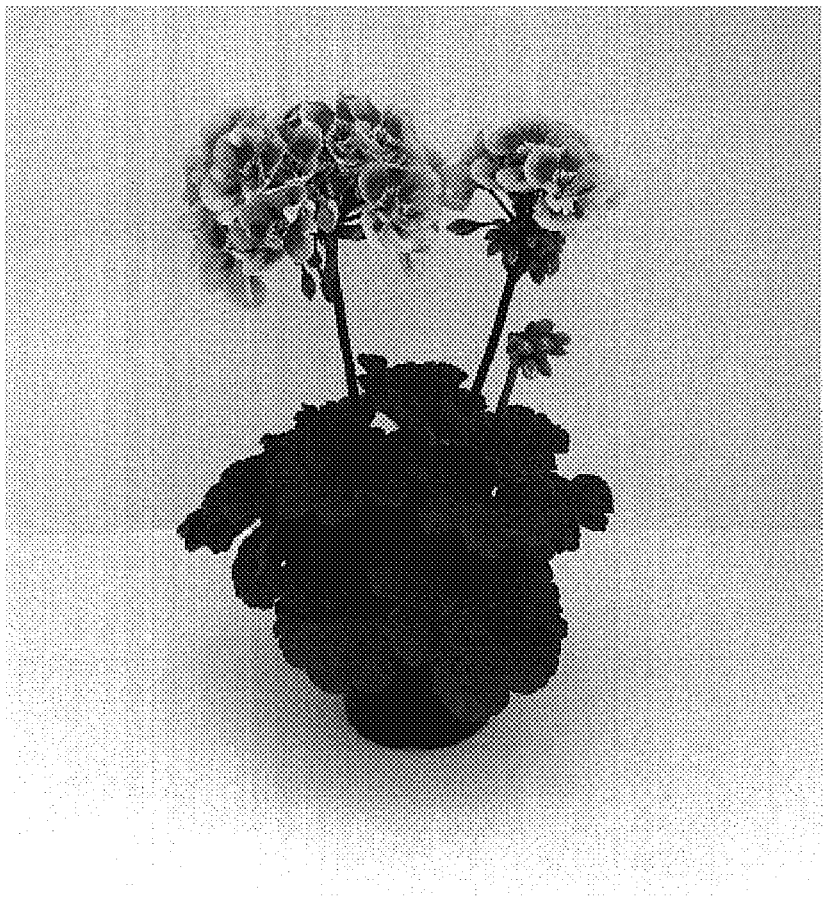
FIG. 1 illustrates a side view of the overall growth and flowering habit of 'Sil Linus'.
Figure 2:
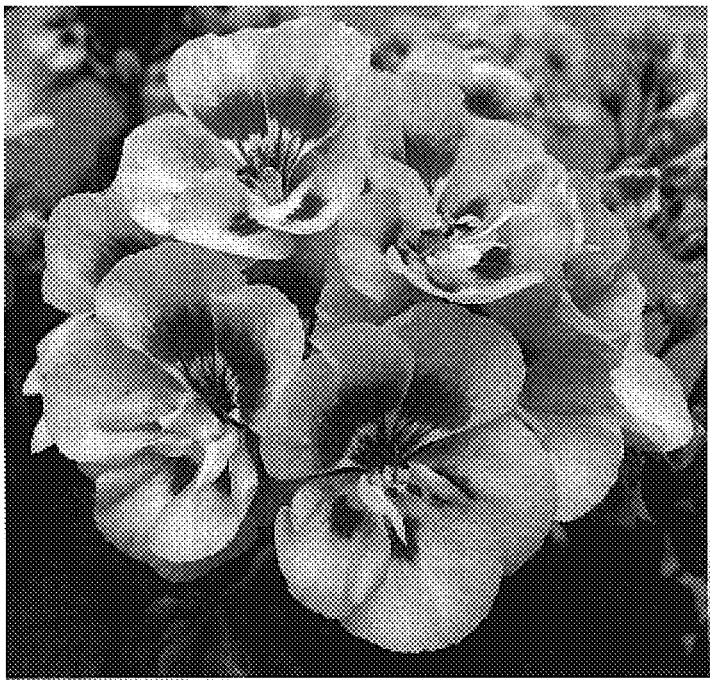
FIG. 2 illustrates a close-up view of an individual umbel of 'Sil Linus'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 25, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 10 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Pelargonium zonale* cultivar Sil Linus.

Parentage:

*Female parent.*—'Kitty', not patented.

*Male parent.*—'Lady', not patented.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Commercial crop time.*—Approximately 8 to 9 weeks from a rooted cutting to finish in a 10 cm pot.

*Growth habit and general appearance.*—Low to moderately vigorous, upright, compact, and bushy.

*Size.*—Height from soil level to top of plant plane: Approximately 24.7 cm. Height from soil level to top of foliage: Approximately 12.2 cm. Width: Approximately 21.3 cm.

*Branching habit.*—Freely branching, pinching enhances basal branching. Quantity of main branches per plant: Approximately 3.

*Branch.*—Strength: Strong. Length: Approximately 4.8 cm. Diameter: Approximately 7.0 mm. Length of central internode: Approximately 8.0 mm. Texture: Densely pubescent with a mixture of glandular and nonglandular hairs. Gland color: Colorless, transparent. Color of young stem: 145C. Color of mature stem: 145B.

Foliage description:

*General description.*—Quantity of leaves per lateral branch: Approximately 7. Fragrance: None. Form: Simple. Arrangement: Opposite.

*Leaves.*—Aspect: petiole is at an acute angle to stem; blade is perpendicular to stem. Shape: Reniform. Margin: Crenate, palmately lobed. Apex: Obtuse. Base: Cordate. Venation pattern: Palmate. Length of mature leaf: Approximately 8.0 cm. Width of mature leaf: Approximately 9.2 cm. Texture of upper surface: Densely pubescent with a mixture of glandular and nonglandular hairs. Texture of lower surface: Pubescent with a mixture of glandular and nonglandular hairs, dense on venation. Gland color: Colorless, transparent. Color of upper surface of young foliage: 137A with venation of 144A. Color of lower surface of young foliage: 138B with venation of 138C. Color of upper surface of mature foliage: Darker than 137A with venation of 144A. Color of lower surface of mature foliage: Between 138B and 138A with venation of 138C.

*Petiole.*—Length: Approximately 7.0 cm. Diameter: Approximately 3.0 mm. Texture: Densely pubescent with a mixture of glandular and nonglandular hairs. Gland color: Colorless, transparent. Color: 144B.

Flowering description:

*Flowering habit.*—'Sil Linus' is freely flowering under outdoor growing conditions with substantially continuous blooming from spring through autumn and year-round in greenhouse environment.

*Lastingness of individual flower on the plant.*—Approximately 12 to 14 days.

Inflorescence description:

*General description.*—Type: Umbel. Positioned above foliage. Quantity of fully open umbels per plant: Approximately 1. Quantity of developing umbels per plant: Approximately: 2. Fragrance: None. Length or height: Approximately 7.8 cm. Width: Approximately 12.4 cm. Quantity of fully open flowers per inflorescence: Approximately 30.

*Peduncle.*—Strength: Strong. Aspect: Erect. Length: Approximately 14.6 cm. Diameter: Approximately 4.5 mm. Texture: Densely pubescent with a mixture of glandular and nonglandular hairs. Gland color: Colorless, transparent. Color: 144A with an overlay of 187B.

Flower description:

*General description.*—Type: Semi-double.

*Bud.*—Rate of opening: Generally takes 3 to 4 days for bud to progress from first color to fully open flower.

*Bud just before opening.*—Shape: Elliptic. Length: Approximately 1.4 cm. Width: Approximately 8.0 mm. Sepal texture: Densely pubescent with a mixture of glandular and nonglandular hairs. Gland color: Colorless, transparent. Petal texture: Glabrous. Petal color: More yellow than N66D.

*Corolla.*—Shape: Round. Diameter: Approximately 5.6 cm. Depth: Approximately 1.1 cm.

*Petals.*—Quantity: Approximately 5 petals and 1 to 2 irregularly-shaped petaloids per flower. Shape: Obovate. Appearance: Dull, Margin: Entire. Apex: Obtuse. Base: Attenuate. Length of upper petals: Approximately 3.3 cm. Width of upper petals. Approximately 2.5 cm. Length of lower petals:

Approximately 3.0 cm. Width of lower petals: Approximately 2.8 cm. Texture of upper and lower surfaces: Glabrous. Color of upper surface of upper petals when fully open: Base of pure white with irregular streaks of N66A, a central spot of N66A, above the central spot a background of 69C with speckles of N66A that fade away toward the margins, and irregular margin areas of lighter than N66D. Color of lower surface of upper petals when fully open: 69D with irregular streaks of N66C at base. Color of upper surface of lower petals when fully open: Base of pure white, a small central spot of N66A, above the central spot a background of 69C with speckles of N66A that fade away toward the margins, and irregular margin areas of lighter than N66D. Color of lower surface of lower petals when fully open: 69D.

*Calyx.*—Shape: 5-pointed star. Diameter: Approximately 2.4 cm.

*Sepals.*—Quantity per flower: Approximately 5. Shape: Lanceolate. Margin: Entire. Apex: Acuminate. Base: Fused. Length of upper sepal: Approximately 1.5 cm. Width of upper sepal: Approximately 5.0 mm. Length of lower sepals: Approximately 1.5 cm. Width of lower sepals: Approximately 3.5 mm. Texture of upper surface: Glabrous. Texture of lower surface: Densely pubescent with a mixture of glandular and nonglandular hairs. Gland color: Colorless, transparent. Color of upper and lower surfaces: 144A with a base of 187B.

*Pedicel.*—Strength: Strong. Aspect: Acute angle to peduncle. Length: Approximately 3.6 cm. Diameter: Approximately 2.0 mm. Texture: Densely pubescent with a mixture of glandular and nonglandular hairs. Gland color: Colorless, transparent. Color: 144A with an overlay of 187B.

*Reproductive organs.*—Androecium: Quantity of mature stamens: Approximately 7 per flower. Anther shape: Oblong. Anther length: Approximately 2.0 mm. Anther color: 187C. Pollen amount: Moderate. Pollen color: 30C. Gynoecium: Pistil quantity: 1 per flower. Pistil length: Approximately 1.2 cm. Stigma shape: 5 branched. Stigma length: Approximately 2.6 mm. Stigma color: 187B. Style length: Approximately 3.4 mm. Style color: 187C. Ovary length: Approximately 5.8 mm. Ovary texture: Densely pubescent. Ovary color: 143A with an overlay of 187A at apex.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Sil Linus', substantially as herein shown and described.

* * * * *